US007494981B2

(12) United States Patent
Johns et al.

(10) Patent No.: US 7,494,981 B2
(45) Date of Patent: Feb. 24, 2009

(54) INHIBITION OF INTERACTION OF PSD93 AND PSD95 WITH NNOS AND NMDA RECEPTORS

(75) Inventors: Roger Johns, Reistertown, MD (US); Yuanxiang Tao, Baltimroe, MD (US)

(73) Assignee: The Johns Hopkins University, Baltimore, MD (US)

( * ) Notice: Subject to any disclaimer, the term of this patent is extended or adjusted under 35 U.S.C. 154(b) by 431 days.

(21) Appl. No.: 10/656,140

(22) Filed: Sep. 8, 2003

(65) Prior Publication Data
US 2005/0119207 A1 Jun. 2, 2005

Related U.S. Application Data

(62) Division of application No. 09/853,895, filed on May 14, 2001, now abandoned.

(60) Provisional application No. 60/242,580, filed on Oct. 23, 2000, provisional application No. 60/203,894, filed on May 12, 2000.

(51) Int. Cl.
*A01N 43/04* (2006.01)
*A61K 31/70* (2006.01)
*C07H 21/02* (2006.01)
*C07H 21/04* (2006.01)

(52) U.S. Cl. .................. 514/44; 536/23.1; 536/24.3; 536/24.33; 536/24.5

(58) Field of Classification Search .................. None
See application file for complete search history.

(56) References Cited

U.S. PATENT DOCUMENTS 5,877,309 A 3/1999 McKay et al.

FOREIGN PATENT DOCUMENTS

| CA | 2273622 | 12/2000 |
|---|---|---|
| WO | WO 97/33173 | 9/1997 |
| WO | WO 97/46877 | 12/1997 |
| WO | WO 99/37768 | 7/1999 |

OTHER PUBLICATIONS

Harris and Lim, J. Cell Science 114: 3219-3231, 2001.*
Stein, C.A., Pharmacol. and Therap. 85: 231-236, 2000.*
Jen et al., Stem Cells 18: 307-319, 2000.*
Chirila et al, January, Biomaterials 23:321-342, 2002.*
Chizh and Headley, Curr. Pharm. Design 11(23): 2977-2994, 2005.*

(Continued)

*Primary Examiner*—Sean McGarry
*Assistant Examiner*—Terra Cotta Gibbs
(74) *Attorney, Agent, or Firm*—Banner & Witcoff, Ltd.

(57) ABSTRACT

PSD-95/SAP90 antisense-treated animals not only experience a significant decrease in MAC for isoflurane, but also experience an attenuation in the NMDA-induced increase in isoflurane MAC. PSD-95/SAP90 appears to mediate the role of the NMDA receptor in determining the MAC of inhalational anesthetics. Suppression of the expression of PSD-95/SAP90 in the spinal cord significantly attenuates responses to painful stimuli mediated through the N-methyl-D-aspartate receptor activation. In spinal cord neurons PSD-95/SAP90 interacts with the N-methyl-D-aspartate receptor subunits 2A/2B. Activation of the N-methyl-D-aspartate receptor in spinal hyperalgesia results in association of the N-methyl-D-aspartate receptor with PSD-95/SAP90. PSD-95/SAP90 is required for hyperalgesia triggered via the N-methyl-D-aspartate receptor at the spinal cord level.

9 Claims, 4 Drawing Sheets

OTHER PUBLICATIONS

Wheal et al, Progress in Neurobiology 55(6), 1998; pp. 611 and 627.*
J. Neurobiology 66(11): 1195-1211, 2006.*
Stathakis et al, Genomics 44(1): 71-82, 1997.*
Manev et al, Life Sciences 76(21): 2403-2407, 2005.*
Tao et al. NeuroReport, 2001 vol. 12:3251-3255.*
Tao et al. Neuroscience, 2000 vol. 98 :201-206.*
Tao et al. Anesthesiology, 2001 vol. 94:1010-1015.*
Agrawal, S. TIBTech, 1996 Voll 14:376-387.*
Agrawal et al. Molecular Medicine Today, 2000 vol. 6:72-81.*
Tamm et al. The Lancet., 2001, vol. 358:489-497.*
Nielsen, PE Gene Therapy, 2005 vol. 12:956-957.*
Woolf C.J., et al., *Pain*, "The induction and maintenance of central sensitization is dependent on N-methyl-D-aspartic acid receptor activiation; implications for the treatment of post-injury pain hypersensitivity states", 44, pp. 293-299 (1991).
Ishizaki, K. et al., *Can. J. Anesth.*, "Intrathecally administered NMDA receptor antagonists reduce the MAC of isoflurane in rats", 43:7, pp. 724-730 (1996).
Sattler, R., et al., *Science*, "Specific coupling of NMDA receptor activation to nitric oxide neurotoxicity by PSD-95 protein", 284, pp. 1845-1848 (1999).
Brenman, J.E., et al., *The Journal of Neuroscience*, "Cloning and characterization of postsynaptic Density 93, a nitric oxide synthase interacting protein", 16(23), pp. 7407-7415 (1996).
Tao, F. et al., *Neuroreport*, "Knockdown of PSD-95/SAP90 delays the development of neuropathic pain in rats", 12:15, pp. 3251-3255 (2001).
Tao, Y-X., et al., *Anesthesiology*, "Effect of the deficiency of spinal PSD95/SAP90 on the minimum alveotar anesthetic concentration of isoflurance in rats", 94:6, pp. 1010-1015 (2001).
Chih-Ling Choi and Scheherazade Sadegh-Nasseri, "HLA-DM Recognizes the Flexible Conformation of Major Histocompatibilty Complex Class II", The Rockefeller University Press, J. Exp. Med.,vol. 192, No. 12, 2000, pp. 1697-1706.
L. N. Maganas and J. S. Trimmer; "Subunit Composition Determines Kv1 Potassium Channel Surface Expression", The Journal of Biological Chemistry, vol. 275, No. 38, 2000, pp. 29685-29693.
Rita Sattler, Zhigang Xiong, Wei-Yang Lu, Mathias Hafner, John F. MacDonald and Michale Tymianski; "Specific Coupling of NMDA Receptor Activation to Nitric Oxide Neurotoxicity by PSD-95 Protein", Science vol. 284, 1999, pp. 1845-1848.
Y.-X. Tao, Y.-Z. Huang, L. Mei and R. A. Johns, "Expression of PSD-95/SAP90 is Critical for N-Methyl-D-Aspartate Receptor-Mediated Thermal Hyperalgesia in the Spinal Cord", Neuroscience, vol. 98, No. 2, 2000, pp. 201-206.
M. Migaud, P. Charlesworth, M. Dempster, L. Webster, A. Watabe, M. Makhinson, Y. He, M. Ramey, R. Morris, J. Morrison, T. O'Dell and S. Grant, "Enhanced Long-Term Potentiation and Imparied Learning in Mice with Mutant Postsynaptic Density-95 Protein", Nature, vol. 396, 1998, pp. 433-439.

Chen et al., "A Safety and Pharmacokinetic Study of a Mixed-Backbone Oligonucleotide (GEM231) Targeting the Type I Protein Kinase A by Two-hour Infusions in Patients with Refractory Solid Tumors," *Clin. Cancer Research 6*, 1259-66, Apr. 2000.
Clark et al., "Clinical use of streptolysin-O to facilitate antisense oligodeoxyribonucleotide delivery for purging autografts in chronic myeloid leukaemia," *Bone Marrow Transplantation 23*, 1303-08, 1999.
Cunningham et al., "A Phase I Trial of c-Raf Kinase Antisense Oligonucleotide ISIS 5132 Administered as a Continuous Intravenous Infusion in Patients with Advanced Cancer," *Clin. Cancer Res. 6*, 1626-31, May 2000.
de Smet et al., "Fomivirsen—a phosphorothioate oligonucleotide for the treatment of CMV retinitis," *Ocul. Immunol. Inflamm. 7*, 189-98, Dec. 1999 (abstract).
Gewirtz, "Myb targeted therapeutics for the treatment of human malignancies," *Oncogene 18*, 3056-62, May 13, 1999 (abstract).
Glover et al., "Phase I Safety and Pharmacokinetic Profile of an Intercellular Adhesion Molecule-1 Antisense Oligodeoxynucleotide (ISIS-2302)," *J. Pharmacol. Exptl. Ther. 282*, 1173-80, 1997.
Nemunaitis et al., "Phase I Evaluation of ISIS 3521, an antisense Oligodeoxynucleotide to Protein Kinase C-Alpha, in Patients with Advanced Cancer," *J. Clin. Oncol. 17*, 3586-95, Nov. 1999.
O'Dwyer et al., "c-*raf*-1 Depletion and Tumor Responses in Patients Treated with the c-*raf*-1 Antisense Oligodeoxynucleotide ISIS 5132 (CGP 69846A)," *Clin. Cancer Res. 5*, 3977-82, Dec. 1999.
Sereni et al., "Pharmacokinetics and tolerability of intravenous trecorvirsen (GEM 91), an antisense phosphorothioate oligonucleotide, in HIV-positive subjects," *J. Clin. Pharmacol 39*, 47-54, Jan. 1999 (abstract).
Stevenson et al., "Phase I clinical/Pharmacokinetic and Pharmacodynamic Trial of the c-*raf*-1 Antisense Oligonucleotide ISIS 5132 (CGP 69846A)," *J. Clin. Oncol. 17*, 2227-36, Jul. 1999.
Waters et al., "Phase I Clinical and Pharmacokinetic Study of Bcl-2 Antisense Oligonucleotide Therapy in Patients With Non-Hodgkin's Lymphoma," *J. Clin. Oncol. 18*, 1812-23, May 2000.
Yuen et al., "Phase I Study of an Antisense Oligonucleotide to Protein Kinase C-α (ISIS 3521/CGP 64128A) in Patients with Cancer," *Clin. Cancer Res. 5*, 3357-63, Nov. 1999.
Bjergård & Dahl, "Solid phase synthesis of oligodeoxyribonucleoside phosphorodithioates from thiophosphoramidites," *Nucl. Acids Res. 19*, 5843-50, 1991.
Hirashima et al., "Artificial Immune System against Viral Infection Involving antisense RNA Targeted to the 5'-Terminal Noncoding Region of Coliphage SP RNA," *J. Biochem. 106*, 163-66 (1989).
Parker et al., "Targeted Gene Walking Polymerase Chain Reaction," *Nucl. Acids Res. 19*, 3055-60, 1991.
Shuttleworth & Colman, "Antisense oligonucleotide-directed cleavage of mRNA in *Xenopus* oocytes and eggs," *EMBO Journal 7*, 427-34, 1988.
Stein & Cohen, "Oligodeoxynucleotides as Inhibitors of Gene Expression: A Review," *Cancer Res. 48*, 2659-68, May 15, 1988.

* cited by examiner

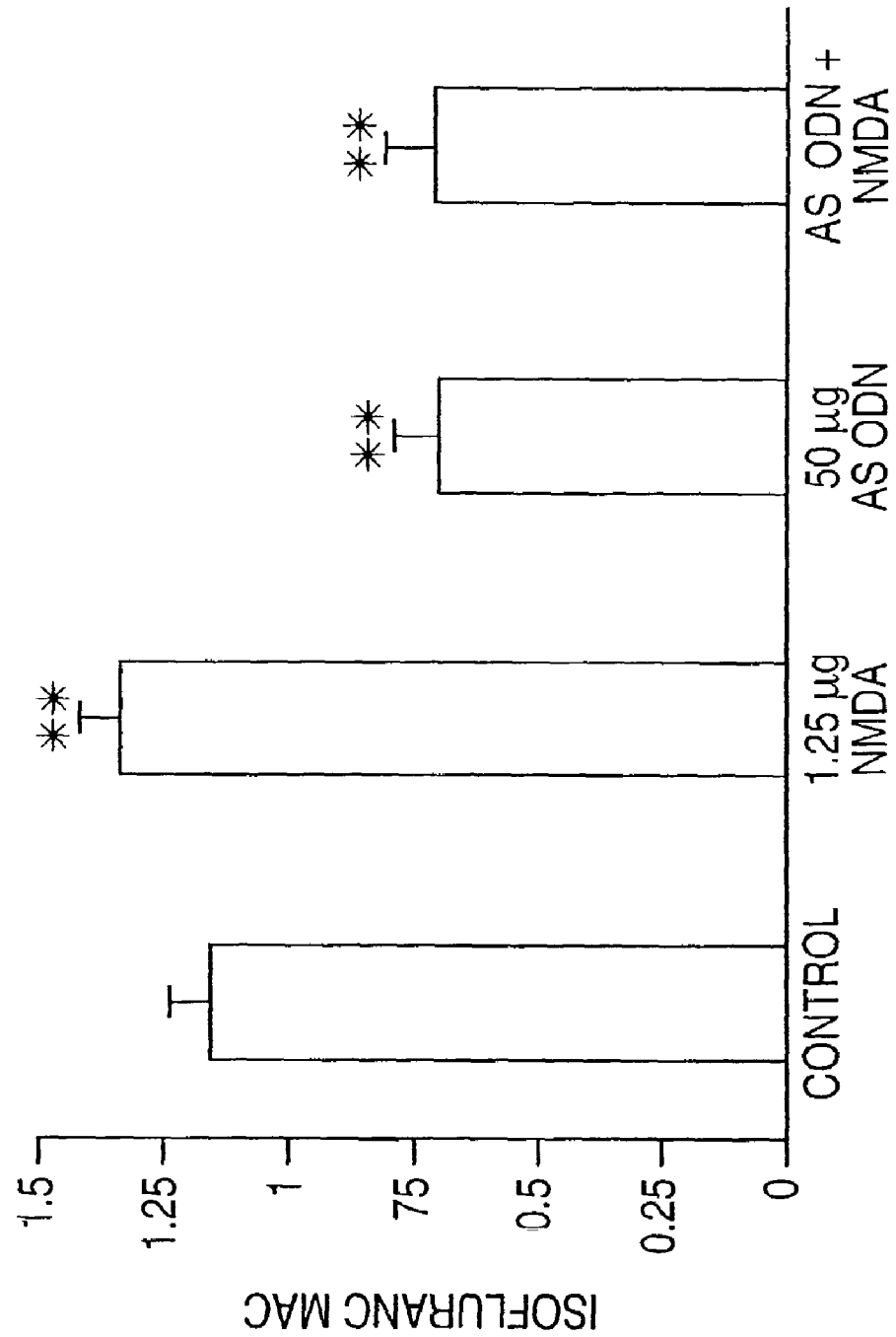

INHIBITION OF INTERACTION OF PSD93 AND PSD95 WITH NNOS AND NMDA RECEPTORS

This application is a divisional of U.S. Ser. No. 09/853,895 filed May 14, 2001 now abandoned. This application claims the benefit of provisional applications Ser. No. 60/242,580 filed Oct. 23, 2000, and Ser. No. 60/203,894 filed May 12, 2000, the entire contents of which are expressly incorporated herein.

This invention was made using funds from the U.S. government under grants from the National Institutes of Health numbered RO GM49111 and RO1 HL39706. The U.S. government therefore retains certain rights in the invention.

BACKGROUND OF THE INVENTION

The potency of anesthetic agents to inhibit the ability of a patient to respond with movement to painful stimuli has long been used as a test of anesthetic action. This potency, characterized by its $ED_{50}$, is widely known as the minimum alveolar concentration (MAC). Several lines of evidence have shown that spinal NMDA receptor activation might play a key role in the processing of nociceptive information[1,29-30] and in the determination of the MAC of inhalational anesthetics.[31-33] For example, the NMDA receptors are distributed mainly in the superficial laminae of the spinal cord.[12,28] Both repetitive C-fiber stimulation and direct application of glutamate or NMDA produce spinal neuronal sensitization and enhance responsiveness, which can be blocked by NMDA receptor antagonists.[1,34-36] Behavioral studies demonstrate that spinal administration of NMDA produces thermal hyperalgesia, caudally directed scratching and biting, and exaggerated responsiveness to light touch.[8,37-39] Moreover, antagonism of the spinal NMDA receptors produces antinociception in numerous animal models of pain[39-44] and reduction in the MAC of isoflurane.[31-33] However, the molecular mechanisms underlying these actions remain unknown.

The postsynaptic density (PSD), a highly organized cytoskeletal structure found adjacent to the postsynaptic membrane of excitatory synapses, is believed to play a role in the organization of receptors and related proteins involved in synaptic signaling.[45-55] A number of proteins enriched in the PSD have been characterized.[47-48] One of these proteins, postsynaptic density-95 (PSD-95)/synapse-associated protein-90 (SAP90), is an abundant scaffolding molecule that binds and clusters the NMDA receptor preferentially at synapses in the brain and spinal cord.[3,4,5,7,9,49] This raises the possibility that PSD-95/SAP90 might be involved in many physiological and pathophysiologic actions triggered via the NMDA and perhaps other receptors in the central nervous system. Indeed, suppression of PSD-95/SAP90 expression attenuated excitotoxicity produced via NMDA receptor activity in brain neurons.[23] The lack of PSD-95/SAP90 revealed an enhanced NMDA-dependent long-term potentiation and impaired learning.[16]

The role of the N-methyl-D-aspartate (NMDA) receptor in spinal hyperalgesia has been demonstrated by behavioral, electrophysiological and neurochemical findings.[1,8,21,26] However, the molecular mechanisms underlying these actions are unclear. The NMDA receptor consists of two distinct types of subunits: NMDAR1 (NR1) and NMDAR2A-D (NR2A-D).[19] The C-termini of the NR2 subunits interact with PSD-95/SAP90 and other members of the membrane-associated guanylate kinase (MAGUK) family in the brain.[2,6,9,10,17,20] This raises the possibility that the sensory hyperalgesia produced through NMDA receptor activation is determined by NMDA receptor-bound proteins of the MAGUK family in the spinal cord.

There is a need in the art for new ways of treating and preventing hyperalgesia and chronic and acute pain. In addition, there is a need in the art for new and safer ways of rendering patients unconscious via general anesthesia or by sedating them.

SUMMARY OF THE INVENTION

One embodiment of the invention provides a method for relieving acute or chronic pain. According to the method an effective amount of an agent which inhibits expression of PSD93 or PSD95 is administered to a subject in need of pain relief. The agent relieves acute or chronic pain experienced by the subject.

Another embodiment of the invention provides a method for treating or preventing hyperalgesia. According to the method an effective amount of an agent which inhibits expression of PSD93 or PSD95 is administered to a subject who has or is at risk of developing hyperalgesia. The administration relieves or prevents hyperlagesia experienced by the subject.

Another aspect of the invention is a method of reducing a threshold for anesthesia. An anesthetic and an agent which inhibits expression of PSD93 or PSD95 are administered to a subject. The amount of anesthetic administered achieves a desired anesthetic effect even though the amount administered is less than the amount required in the absence of the agent to achieve the desired anesthetic effect. This minimizes the serious side effects of the anesthetics including cardovascular and respiratory depression.

The present invention also provides an isolated and purified antisense polynucleotide which is complementary to PSD95 or PSD93 mRNA.

Another embodiment of the invention is a method for relieving acute or chronic pain. An effective amount of an agent which inhibits interaction of a first protein selected from the group consisting of PSD93 and PSD95, with a second protein selected from the group consisting of nNOS and NMDA receptor, is administered to a subject in need thereof. The agent does not cause cardiovascular or respiratory depression. The administration relieves acute or chronic pain experienced by the subject.

Also provided is an alternative method for treating or preventing hyperalgesia. An effective amount of an agent which inhibits interaction of a first protein selected from the group consisting of PSD93 and PSD95, with a second protein selected from the group consisting of nNOS and NMDA receptor, is administered to a patient experiencing hyperalgesia or who is at risk of developing hyperalgesia. The agent does not cause cardiovascular or respiratory depression. Hyperalgesia experienced by the subject is relieved or prevented by the administration.

Also provided by the present invention is a method of reducing a threshold for anesthesia. An anesthetic and an agent which inhibits interaction of a first protein selected from the group consisting of PSD93 and PSD95, with a second protein selected from the group consisting of nNOS and NMDA receptor, are administered to a subject. The agent does not cause cardiovascular or respiratory depression. The amount of anesthetic administered is less than the amount required in the absence of the agent to achieve a desired anesthetic effect. The desired anesthetic effect is thus achieved.

The present invention also provides a method of anesthetizing a subject. An agent which inhibits expression of PSD93 or PSD95 is administered to a subject. The agent renders the subject unconscious or sedated.

Another embodiment of the invention provides a method of anesthetizing or sedating a subject. An agent which inhibits interaction of a first protein selected from the group consisting of PSD93 and PSD95, with a second protein selected from the group consisting of nNOS and NMDA receptor, is administered to a patient. The agent does not cause cardiovascular or respiratory depression. The agent renders the subject unconscious or sedated.

Yet another aspect of the invention is a method of screening for substances useful for relieving pain or inducing unconsciousness or sedation. A test substance is contacted with a first protein and a second protein under conditions where the first protein and the second protein bind to each other. The first protein is selected from the group consisting of PSD93, PSD95, and a combination thereof. The second protein is selected from the group consisting of nNOS, NMDA receptor, NR2A subunit, NR2B subunit, and combinations thereof. The mixture of proteins is assayed to determine the binding of the first protein to the second protein. Any parameter which reflects that binding can be assayed. Such parameters include the amount of free nNOS, the amount of free PSD93, the amount of free PSD95, the amount of free NMDA receptor, the amount of free NR2A subunit, the amount of free NR2B subunit, the amount of bound nNOS, the amount of bound PSD93, the amount of bound PSD95, the amount of bound NMDA receptor, the amount of bound NR2A subunit, the amount of bound NR2B subunit and combinations of them. A test substance which increases the amount of free nNOS, free PSD93, free PSD95, free NMDA receptor, free NR2A subunit, or free NR2B subunit, or which decreases the amount of bound nNOS, bound PSD93, bound PSD95, bound NMDA receptor, bound NR2A subunit, or bound NR2B subunit is identified as a candidate drug for relieving pain or inducing unconsciousness or sedation.

BRIEF DESCRIPTION OF THE DRAWINGS

In FIG. 1Aa, immunoblot showing the expression of PSD-95/SAP90 in the PSD fractions of the spinal cord (SC), dorsal root ganglion (DRG) and other brain regions (as positive controls) in the normal rats. HI: hippocampus; CO: cortex; CE: cerebellum. In FIG. 1Ab, immunoblot showing representative effects of PSD-95/SAP90 antisense (AS), missense (MS) and sense (SE) ONDs, as well as saline (SA), on the expression of PSD-95/SAP90, nNOS and NR2A/2B in the spinal cord. PC: positive control tissue from hippocampus. Asterisk: non-specific band by the secondary antibody, useful to control for protein loading and blot exposure times. In FIG. 1B, RT-PCR analysis showed that 0.737 Kb mRNA was detected in the spinal cord and other brain regions (hippocampus, cortex, cerebellum and brainstem), but not in muscle. PCR product was directly cloned into the TA cloning vector and verified as PSD-95/SAP90 by automatic DNA sequencing. β-actin mRNA was used as a loading control.

FIGS. 2A and 2B. Distribution of PSD-95/SAP90 immunoreactivity in lumbar enlargement segments of the spinal cord. The PSD-95/SAP90 immunoreactivity was localized mainly in lamina I and outer lamina II (A). Under high magnification, many PSD-95/SAP90 immunoreactive puncta were observed (B). Scale bars: 200 μM in A; 40 μm in B.

FIG. 4. Effect of intrathecal administration of NMDA on isoflurane MAC in the saline- and PSD-95/SAP90 antisense ODN-treated groups. Data are presented as mean±SD. n=5 animals for each group, except n=14 for the saline-treated (control) group. ** Significantly different from control (P<0.01).

DETAILED DESCRIPTION OF THE INVENTION

Figure 1A:
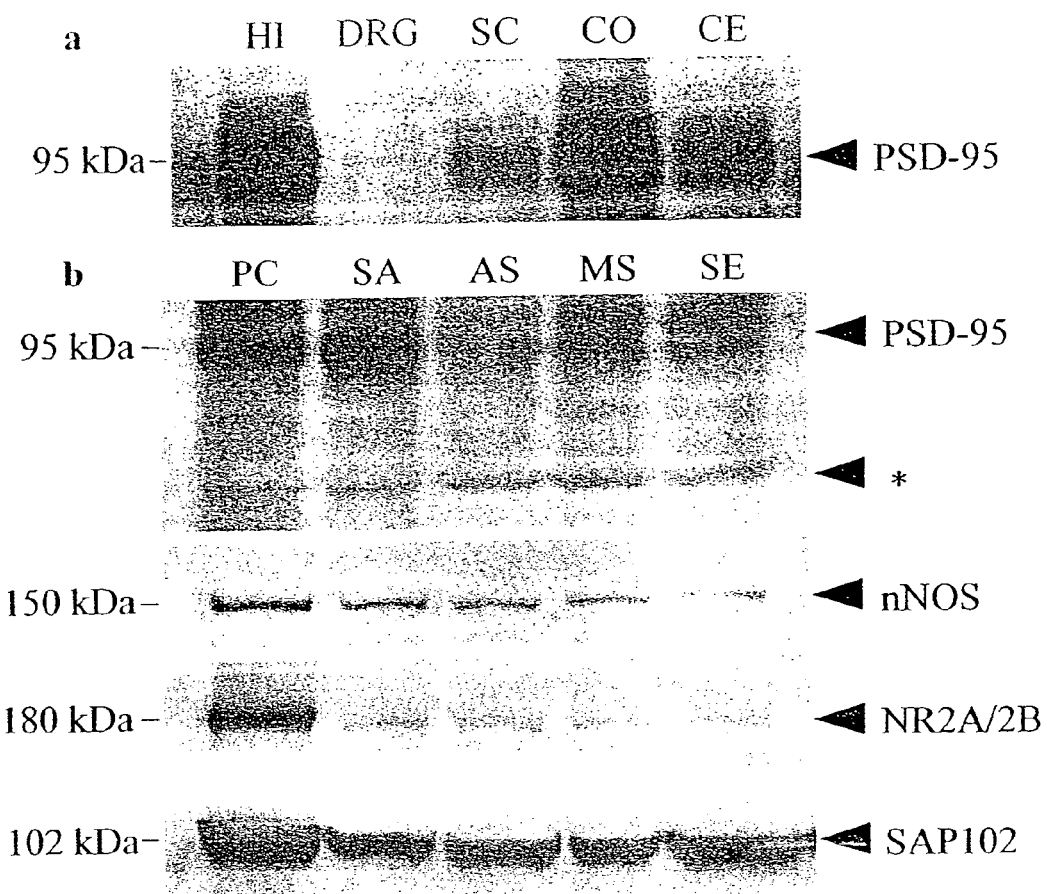
FIGS. 1A and 1B. Expression of PSD-95/SAP90 mRNA and protein in the spinal cord.

It is a discovery of the present inventors that PSD95 and PSD93 mediate the interaction of NMDA receptors and nNOS in the spinal cord, and are involved in generating responses to painful stimuli. The inventors have found that inhibition of the interaction of NMDA receptors and nNOS via PSD95 and PSD93 can attenuate responses to painful stimuli, as well as lower thresholds for anesthetics. Moreover, we have found that inhalational anesthetics themselves inhibit the interaction of NMDA receptors and nNOS via PSD95 and PSD93. Thus new and improved anesthetics and sedatives can be identified using the identified interaction as an assay system.

Acute or chronic pain can be relieved or prevented according to the present invention by administering to a subject an effective amount of an agent which inhibits expression of PSD93 or PSD95. The agents of the present invention also can be used to treat or prevent hyperalgesia, as well as to reduce a threshold for anesthesia. The agent used can be an antisense oligonucleotide (ODN) which is complementary to mRNA encoding PSD93 or PSD95. Preferably the antisense oligonucleotide is complementary to nucleotides encoding a PDZ domain. More preferably the antisense oligonucleotide is complementary to nucleotides 241 to 258 of PSD95. Any agent which acts to specifically inhibit transcription or translation of PSD93 or PSD95 can be used. Oligonucleotides useful in the invention can be naked oligonucleotides or can be administered in a vector, liposome, particle or other protective formulation. If in a vector, the vector can express RNA molecules which are complementary to the native PSD93 or PSD95 mRNAs. Also encompassed by the present invention are oligonucleotides which contain nucleotide analogue moieties to render the oligonucleotides less susceptible to enzymatic degradation. Suitable nucleotide analogue moieties are known in the art and include phophorothioates.

Agents according to the present invention can be administered any way known in the art which is convenient and efficient for the particular agent and the application. Preferably the agent is administered intrathecally, per os, or intravenously. However, other means can be used as appropriate, including subdermal, subcutaneous, rectal, intraperitoneal, subarachnoid, caudal, epidural, inhalational, and intramuscular administrations. Anesthetics and sedatives used in the methods of the present invention can also be administered by any of these same means. Preferred anesthetics according to the invention are inhalational anesthetics, including halothane, isoflurane, desflurane, xenon, and sevoflurane.

Compositions are provided for inhibiting expression of PSD95 or PSD93. Such compositions comprises an isolated and purified antisense polynucleotide which is complementary to PSD95 or PSD93 mRNA. Preferably the polynucleotide is complementary to nucleotides encoding a PDZ domain. Any of the three such domains can be targeted, although the third such domain, i.e., the C-terminal PDZ domain, may be the most effective. One particular oligonucleotide which has been found to be effective is complementary to nucleotides 241 to 258 of PSD95. The analogous nucleotides of PSD93 can also be used. The polynucleotide can be formulated in a pharmaceutically acceptable vehicle so that it can be used to prevent pain or to lower an anesthetic or sedative threshold. Particular vehicles which are suitable for intrathecal or inhalational therapy can be advantageously used. The formulations can be in liquid or vapor form. They can be vaporized by bubbling a gas through them. Preferably the formulations of the invention will be manufactured under regulatory-approved conditions for administration to humans. Requirements for such formulations typically include sterility and freedom from pyrogens.

Not only can agents which specifically inhibit the expression of PSD93 or PSD95 be used in the methods of the present invention, but also agents which inhibit the interaction of PDS93 or PSD95 with either nNOS or NMDA receptors. Such agents can be used for the same purposes as discussed above, for relieving acute or chronic pain, for reducing the threshold for anesthetics and sedatives, and for anesthetizing and sedating patients directly. Agents useful according to the present invention do not cause cardiovascular or respiratory depression. Such agents can be administered to the same populations of patients as discussed above, i.e., those in need of anesthesia, those in need of relief from chronic or acute pain, and those who experience hyperalgesia or are at risk of developing hyperalgesia. Such patients include those whose pain is mechanical, thermal, neuropathic, or inflammatory in origin.

Protein interaction-inhibitory agents of the invention preferably bind to a PDZ domain of any of the binding participants, including nNOS, NMDA receptors, PDS93 or PDS95. Typically and preferably the agent does not impair motor function, i.e., locomotion. Such agents can be identified by any of a number of screening techniques which rely on the inhibition of expression or interactions of PDS93 or PDS95. Generally, test substances are contacted with a first protein and a second protein under conditions where the first protein and the second protein bind to each other. The first protein is PSD93, PSD95, or a combination the two proteins. The second protein can be nNOS, NMDA receptor, NR2A subunit, NR2B subunit, or combinations of these proteins. Fusion proteins which contain all or relevant binding portions of these proteins can be used, as is desirable for ease of detectability or purification and handling. The amount of protein which is bound or free in the presence and absence of the test substance can be determined by any techniques known in the art. Test substances which increase the amount of free binding partners or which decrease the amount of bound binding partners are identified as candidate drugs for relieving pain or inducing unconsciousness or sedation.

Many protein-protein binding assays are known in the art and any such format or technique can be used as is convenient. In some assays the proteins are contacted in vitro. In other assays the proteins are in yeast cells containing recombinant forms of the first and second proteins, and the test substance is contacted with the whole yeast cells. Such assays include the well-known two hybrid assays, in which binding of two binding partners reconstitutes a transcriptional activating activity. In these assays the first and second binding partners are each fused to a first and second yeast protein which reconstitute a functional transcriptional activator when brought into physical proximity by binding of the first recombinant protein to the second recombinant protein. Colorimetric, enzymatic, or growth assays can be used to determine the transcriptional activation reconstitution. Candidates which are identified as having inhibitory activity in such assays can be further tested in an animal to determine if the candidate drug relieves pain or induces unconsciousness or sedation.

PSD-95/SAP90 antisense-treated animals not only experience a significant decrease in MAC for isoflurane, but also experience an attenuation in the NMDA-induced increase in isoflurane MAC. PSD-95/SAP90 appears to mediate the role of the NMDA receptor in determining the MAC of inhalational anesthetics. Suppression of the expression of PSD-95/SAP90 in the spinal cord significantly attenuates responses to painful stimuli mediated through the N-methyl-D-aspartate receptor activation. In spinal cord neurons PSD-95/SAP90 interacts with the N-methyl-D-aspartate receptor subunits 2A/2B. Activation of the N-methyl-D-aspartate receptor in spinal hyperalgesia results in association of the N-methyl-D-aspartate receptor with PSD-95/SAP90. PSD-95/SAP90 is required for hyperalgesia triggered via the N-methyl-D-aspartate receptor at the spinal cord level.

The pretreatment of PSD-95/SAP90 antisense ODN but not sense or missense ODN produced a remarkable reduction in isoflurane MAC. This was not accompanied by changes in ether blood pressure or heart rate. Furthermore, the PSD-95/SAP90 antisense ODN blocked NMDA-induced increase in isoflurane MAC. The deficiency of PSD-95/SAP90 expression may produce anesthetic and analgesic actions at the spinal cord level and PSD-95/SAP90 might mediate the role of the NMDA receptor in determining the MAC of inhalational anesthetics.

Antisense ODNs have been widely used as research tools, and even as drugs in clinical trials. Antisense ODNs inhibit protein expression by the mechanisms of (1) steric blockade of ribosomal subunit attachment to mRNA at the 5' cap site; (2) interference with proper mRNA splicing through antisense binding to splice donor or splice acceptor sites; (3) RNase-H-mediated degradation of hybridized mRNA.[18] The proper design and controls of experiments are critical in demonstrating a true antisense effect. The specificity of intrathecal treatment with PSD-95/SAP90 antisense ODN has been shown. First, we designed the standard controls of equivalent sense sequence and missense ODNs. Neither had any effect on the isoflurane MAC. This indicates the specificity of the inhibition observed with the antisense ODN. Second, all of the ODNs had been searched to exclude non-specificity of the sense or antisense ODNs and to show that missense ODN did not match any confounding sequences in the GenBank database. Moreover, our previous results have demonstrated that antisense ODNs only suppressed the expression of PSD-95/SAP90 but not the expression of NMDA receptor subunits NR2A/2B, neuronal nitric oxide synthase or SAP102 (a protein that is closely related to the targeted protein) in the spinal cord.[49] The effects observed following treatment with the PSD-95/SAP90 antisense ODN are unlikely to be explained by changes in the expression of other proteins. Finally, the antisense ODNs at the doses used only affected isoflurane MAC without untoward effects in any of the treated animals including the antisense groups. Considering these several lines of evidence, we believe that the effects we have described may be due to a direct and selective interference of the antisense ODN with mRNA transcripts of PSD-95/SAP90 and to the blockade of protein production via binding to the nucleotides of PSD-95/SAP90 mRNA.

The regional expression and function of PSD-95/SAP90 in the mammalian brain have been investigated using a variety of experimental approaches.[3,4,5,7,9] PSD-95/SAP90 immunoreactivity was found mainly in cortex, hippocampus and cerebellum.[54-56] In brain neurons, suppression of PSD-95/SAP90 expression that selectively disrupted physical linkage of the NMDA receptor with neuronal nitric oxide synthase has been demonstrated to attenuate excitotoxicity and Ca2+-activated nitric oxide production via NMDA receptor activity.[23] Mice carrying a targeted mutation in the PSD-95/SAP90 gene showed an enhanced NMDA-dependent long-term potentiation and impaired learning.[16] Recently, we found that PSD-95/SAP90's mRNA and protein also were enriched in the spinal cord and selectively distributed in the superficial dorsal horn, where PSD-95/SAP90 expression overlapped with that of the NMDA receptor.[12,28] In the spinal neurons, PSD-95/SAP90 interacted with the NMDA receptor subunits 2A/2B.[49] Behavioral studies showed that intrathecal administration of antisense ODN for PSD-95/SAP90 significantly attenuated facilitation of the tail-flick reflex triggered through the NMDA receptor activation.[49] The evidence above indicates that activation of the NMDA receptor in spinal hyperalgesia results in association of the NMDA receptor with PSD-95/SAP90 and that PSD-95/SAP90 is required for the spinal mechanisms of hyperalgesia. This suggests that PSD-95/SAP90 may be involved in the processing of pain and that deficiency of PSD-95/SAP90 may produce analgesic action at the spinal cord level. Such an action is consistent with the effect of the deficiency of PSD-95/SAP90 on MAC. Doses of antisense ODNs did not cause motor and general behavioral dysfunction when administered intrathecally in rats. The effect of suppression of spinal PSD-95/SAP90 expression that resulted in the reduction in MAC may be due to effects on analgesia alone. However, PSD-95/SAP90 has been demonstrated to be involved in the mechanisms of long-term potentiation and learning.[16] An effect of antisense ODN on righting reflex was not observed. The possibility of these actions of the antisense ODNs in the central nervous system could not be ruled out from the current study since the intrathecal antisense effect had a segmental nature.

A role for the NMDA receptors in determining the MAC of inhalational anesthetics is suggested by the fact that the systemic or intrathecal administration of NMDA antagonists significantly reduces the MAC of isoflurane in rats, which is completely reversed to control level by intrathecal administration of NMDA.[31-33] The current study further indicated that intrathecal administration of NMDA increased the MAC of isoflurane in saline-treated rats. Interestingly, in antisense ODN-treated rats, intrathecal injection of NMDA did not affect the MAC of isoflurane. PSD-95/SAP90 localization completely overlapped with the NMDA receptor subunits 2A/2B in spinal superficial dorsal horn.[49] Furthermore, the PSD-95/SAP90 antibody was able to immunoprecipitate not only PSD-95/SAP90 but also NR2A/2B in vivo.[49] These findings demonstrate that PSD-95/SAP90 interacts with NR2A/2B in the spinal cord in vivo. Combined with the current results, it is suggested that PSD-95/SAP90 is essential for the actions of the NMDA receptor in determining the MAC of inhalational anesthetics.

In our experiments, no significant hemodynamic effects were observed in the ODN-treated animals during isoflurane anesthesia. However, intrathecal administration of NMDA resulted in a significant increase in systolic and diastolic blood pressure during isoflurane anesthesia in both the saline- and antisense ODN-treated groups. It has been demonstrated that sympathetic preganglionic neurons located in the intermediate nucleus of the spinal cord are integral elements in the neural pathway linking the central nervous system to sympathetic nerves supplying the heart and blood vessels.[57,58] The effects of NMDA on blood pressure may be due to the involvement of the NMDA receptor in regulation of sympathetic output at the spinal cord level. In immunohistochemical studies, glutamate and its receptors were found in the intermediolateral nucleus of the thoracic spinal cord.[59,60] Intrathecal administration of NMDA at the T10 level increased arterial pressure. This action was blocked by NMDA receptor antagonists.[61,62] It is likely that NMDA, administered intrathecally at the lumbar level, activates spinal sympathetic activity in the intermediolateral nucleus and produces the increase in blood pressure. The antisense ODNs had no effect on the hemodynamics or on the NMDA-induced increase in blood pressure, a finding which is consistent with our previous observation that PSD-95/SAP90 was absent or present at extremely low levels in the intermediolateral nucleus of the spinal cord.[49] It could be that the second message signaling pathways in the somatic and the sympathetic nervous systems are different with respect to the NMDA receptor. Hong et al[61] and West et al[62] reported that microinjection of NMDA into the intermediolateral nucleus at the spinal $T_2$ level or intrathecal injection of NMDA at the $T_{10}$ level produced an increase in heart rate. Interestingly, the effect of NMDA on heart rate was not observed in either saline- or antisense ODN-treated groups in the present study. The reason for this discrepancy between the previous and the present studies is not clear and may be due to a difference in anesthetic agents (isoflurane in the present study vs urethane, chloral hydrate and sodium pentobarbitone). It is interesting to note that intrathecal administration of the NMDA receptor antagonist, APV, produced a dose-related decrease in arterial pressure but not in heart rate.[61,63] These data suggest that there is a tonic activation of the NMDA receptor in the spinal sympathetic pathway to the vessels but not to the heart.

MAC for isoflurane was significantly decreased and the NMDA-induced increase in isoflurane MAC was attenuated in the PSD-95/SAP90 antisense-treated animals. The binding of PSD-95/SAP90 to the NMDA receptor preferentially at synapses in the spinal cord and brain suggests that PSD-95/SAP90 may mediate the role of the NMDA receptor in determining the MAC of inhalational anesthetics.

EXAMPLES

Example 1

This example demonstrates that PSD-95 is necessary for thermal hyperalgesia.

To examine whether PSD-95/SAP90 was required for thermal hyperalgesia triggered through NMDA receptor activation, we made an antisense oligonucletide (OND) corresponding to the PDZ domain nucleotides 241 to 258 (5'-TGTGATCTCCTCATACTC-3'; SEQ ID NO: 1) of rat PSD-95/SAP90 mRNA, as well as the sense OND and missense OND (5'-AAGCCCTTGTTCCCATTT-3'; SEQ ID NO: 2). All of the ONDs were compared to the Gene Bank database (GenBank accession number M96853) and found not to be complementary to any registered nucleotide sequences. The effects of antisense, sense and missense ONDs on baseline and NMDA-induced tail-flick latencies were assessed. Consistent with previous studies,[14,15,24,26] intrathecal administration of NMDA at 5 nM/10 μl (n=6) (data not shown) or 10 nM/10 μl (n=12) induced a facilitation of the tail-flick reflex (The baseline tail-flick latency was reduced from 6.58±0.57 to 4.88±0.41 seconds. p<0.01) (Table 1). We found that the NMDA-produced facilitation of the tail-flick reflex was attenuated in rats pretreated with antisense ONDs (25 μg/10 μl and 50 μg/10 μl every 24 h for 4 days; n=6 each group) but not in those pretreated with sense OND (50 μg/10 μl every 24 h for 4 days; n=6) or missense OND (50 μg/10 μl every 24 h for 4 days; n=6) (Table 1). Antisense OND given intrathecally at 25 and 50 μg dramatically prevented the NMDA-induced decrease of the tail-flick latency by 55% (p<0.05) and 82%

(p<0.01), respectively. When these rats treated with antisense OND were allowed to recover for an additional four days, their tail flick latency in response to NMDA stimulation returned to normal. To identify that NMDA-induced thermal hyperalgesia was produced specifically through NMDA receptor activation but not non-NMDA receptor activation, we observed the effects of a selective NMDA receptor antagonist, MK-801, and a selective non-NMDA receptor antagonist, DNQX, on NMDA-induced facilation of the tail-flick reflex. As shown in Table 1, intrathecal MK-801 at 10 nM/10 µl (n=6) completely abolished facilitation of the tail-flick reflex stimulated by NMDA (p<0.01), while intrathecal DNQX at 20 nM/10 µl (n=6) had no effect (p>0.05). The baseline thermal reflex is generally considered to be mediated via non-NMDA receptor mechanisms.[13-15,26] Antisense OND for PSD-95/SAP90 did not affect baseline tail-flick latency (percentage change of TF latency was 0.44±1.95) compared to the control group; Nor did sense and missense ONDs (percentage changes of TF latencies were −0.82±1.94 and −2.05±1.57, respectively). In addition, motor weakness or dysfunction was not observed in locomotor tests (including placing reflex, grasping reflex and righting reflex) in any of the treated animals including the antisense groups (data not shown).

Example 2

This example shows that PSD-95 antisense oligonucleotide acts specifically to inhibit PSD-95 expression.

Antisense ONDs, widely used as research tools and even as drugs in clinical trials, inhibit protein expression by the mechanisms of (1) steric blockade of ribosomal subunit attachment to mRNA at the 5' cap site; (2) interference with proper mRNA splicing through antisense binding to splice donor or splice acceptor sites; (3) Rnase-H-mediated degradation of hybridized mRNA.[18] To further examine whether the action of antisense OND for PSD-95/SAP90 above was specifically due to selective decrease or lack of PSD-95/SAP90 but not other proteins in the spinal cord, we detected PSD-95/SAP90, NMDA receptor subunits 2A/2B (NR2A/2B), neuronal nitric oxide synthase (nNOS) and SAP-102 in homogenates from crude lumbar enlargement segments in the normal, saline-treated (control) and OND-treated rats. PSD-95/SAP90 protein was enriched in the postsynaptic density (PSD) fraction of the spinal cord in normal, control, sense OND- and missense OND-treated groups (FIG. 1A a and b). In contrast, in the antisense OND-treated group, PSD-95/SAP90 expression was suppressed to <15% of control (FIG. 1Ab). No significant change in expression of NR2A/2B, nNOS and SAP-102 was found in normal, control or OND-treated animals (FIG. 1Ab). It is likely that the antisense OND for PSD-95/SAP90 selectively interferes with mRNA transcription of PSD-95/SAP90 and blocks production of the protein via binding to the nucleotides of PSD-95/SAP90 mRNA. Combined with the behavioral results above, it is suggested that the expression of PSD-95/SAP90 in the spinal cord might be critical for spinal thermal hyperalgesia via NMDA receptor activation.

Example 3

This example demonstrates the expression and localization of PSD95 in the spinal cord, as well as the colocalization with NMDA receptors and nNOS.

Figure 1B:
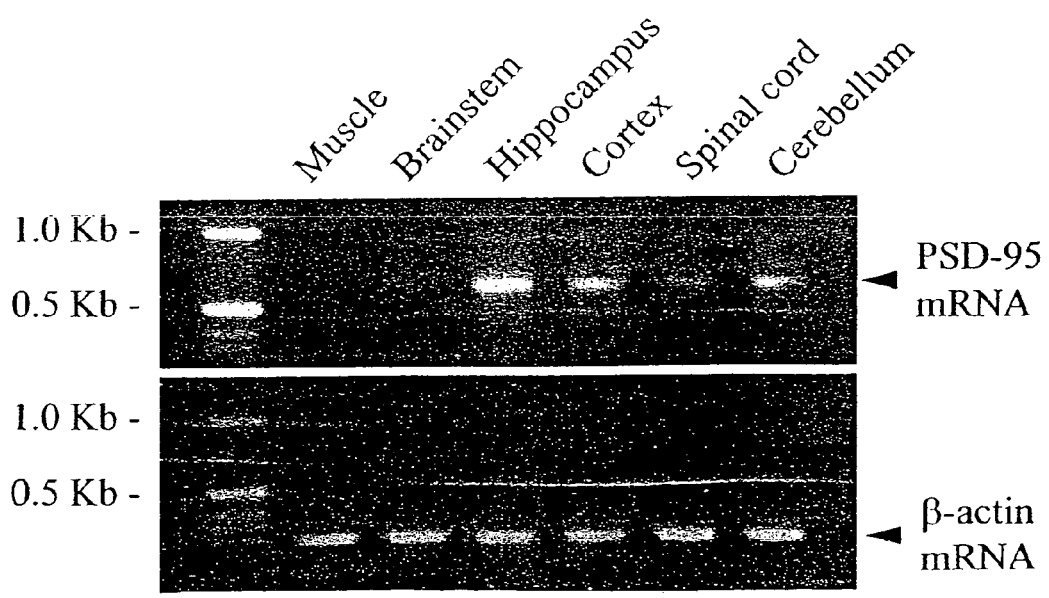
Figure 3:
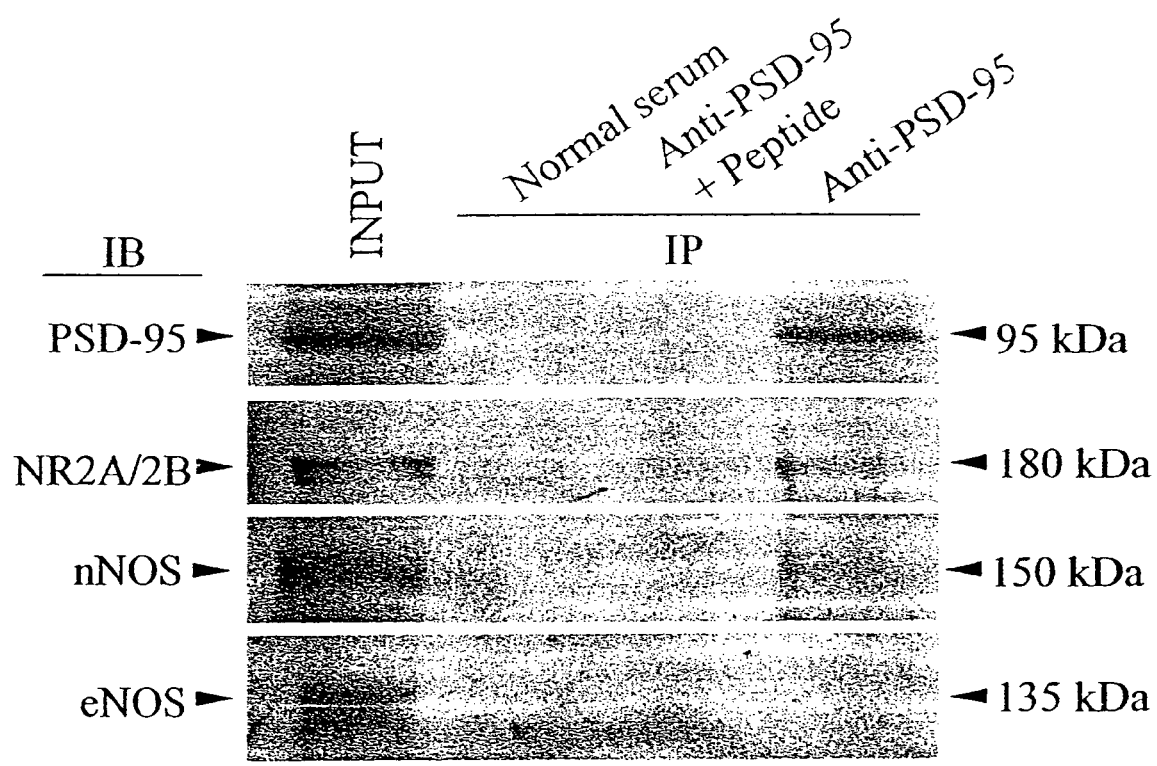
FIG. 3. Identification of a ternary complex assembled by PSD-95/SAP90 with NR2A/2B and nNOS in the spinal cord neurons. PSD-95/SAP90 antibody immunoprecipitated not only PSD-95/SAP90 but also NR2A/2B and nNOS. In contrast, endothelial NOS (eNOS) was not immunoprecipitated by PSD-95/SAP90 antibody. Ten μg protein was loaded in INPUT lane and 100 μg in other lanes.

To provide further support for the role of PSD-95/SAP90 in spinal hyperalgesia, we examined the expression of PSD-95/SAP90 and the interaction of PSD-95/SAP90 with the NMDA receptor in the spinal cord. The regional expression and function of PSD-95/SAP90 in the mammalian brain have been investigated using a variety of experimental approaches.[3-5,7,9,16] To our knowledge, however, there are no previous reports of its expression or function in adult spinal cord. Thus, RNA for messages encoding the PSD-95/SAP90 protein was extracted from tissues of the spinal cord, other regions of the brain (as positive controls), and muscle (as a negative control). This RNA was probed with the use of RT-PCR analysis. A 0.735 Kb mRNA was detected in the spinal cord and regions of brain (hippocampus, cortex, cerebellum and brainstem), but not in muscle (FIG. 1B). The PCR product then was directly cloned into the TA cloning vector and verified as PSD-95/SAP90 by automatic DNA sequencing. Furthermore, the distribution of PSD-95/SAP90 immunoreactivity in the spinal cord was observed. As illustrated in FIG. 2A, PSD-95/SAP90 immunoreactivity was found in the spinal cord and distributed mainly in lamina I and outer lamina II. Under high magnification, many PSD-95/SAP90 immunoreactive puncta were observed (FIG. 2B). The superficial dorsal horn not only contains many interneurons and their processes but also receives the processes from the deep dorsal horn neurons, the primary afferent termini from the periphery and the descending fibers from supraspinal structures.[22] Since PSD-95/SAP90 is specifically localized at synapses and has been found both pre- and post-synaptically in the brain,[3,4] we investigated the sources of PSD-95/SAP90 immunoreactive puncta in the superficial dorsal horn. In the dorsal root ganglion of normal rat, no PSD-95/SAP90 protein was detected (FIG. 1Aa). Also, there was no change in the density of PSD-95/SAP90 immunoreactivity in the superficial dorsal born after unilateral spinal nerve cut or bilateral dorsolateral fasciculi cut (data not shown). More importantly, PSD-95/SAP90 mRNA was detected and PSD-95/SAP90 expression from antisense OND-treated rats was significantly suppressed in the spinal cord as described above. These data indicate that PSD-95/SAP90 in the superficial dorsal horn, to a great extent, is intrinsic to the spinal cord. The superficial dorsal horn is the primary center for processing noxious stimulation.[22] The area-specific expression and distribution of PSD-95/SAP90 in the spinal cord suggest that PSD-95/SAP90 has important implications for the mechanisms of nociceptive processing at the spinal cord level. The NMDA receptor has been demonstrated to mainly locate in lamina I and outer lamina II of the spinal cord.[12,28] Combined with the present data, the NMDA receptor completely overlapped with PSD-95/SAP90 in the spinal dorsal horn. It is suggested that PSD-95/SAP90 may co-localize and interact with the NMDA receptor in the spinal cord neurons. This was further confirmed with the use of co-immunoprecipitation, demonstrating that the PSD-95/SAP90 antibody was able to immunoprecipitate not only PSD-95/SAP90 but also NR2A/2B and nNOS in vivo (FIG. 3). In contrast, endothelial NOS (eNOS) was not immunoprecipitated with the PSD-95/SAP90 antibody (FIG. 3). These findings show that PSD-95/SAP90 interacts with NR2A/2B in the spinal cord in vivo, suggesting that glutamate stimulation of the NMDA receptor in the spinal cord may result in association of the NMDA receptor with PSD-95/SAP90 protein in spinal hyperalgesia.

Example 4

This example describes the experimental procedures used in the experiments described in the examples 1-3.

Animal preparation and behavioral testing. All experiments were carried out with the approval of the Animal Care Committee at the Johns Hopkins University and were consistent with the ethical guidelines of the National Institutes of Health and the International Association for the Study of Pain. Male Sprague-Dawley rats (250-300 g) were implanted with an intrathecal PE-10 catheter into the subarachnoid space at the rostral level of the spinal cord lumbar enlargement through an incision at the atlanto-occipital membrane according to the method as described.[25,27] One week or more later, the rats were injected intrathecally with saline or ONDs every 24 h for 4 days. On the fifth day, saline, NMDA, MK-801+NMDA or DNQX+NMDA was given intrathecally. Nociception was evaluated by the radiant heat tail-flick test. The doses and time point of maximal effect of NMDA used in the present study were determined based on a previous study.[24] The tail-flick apparatus (Model 33B Tail Flick Analgesy Meter, IITC Life Science, Woodland Hills, Calif., USA) generated a beam of radiant heat that was focused on the underside of the tail, 5 cm from the tip. A cut-off time latency of 13.5 s was used to avoid tissue damage to the tail. Nociception was assessed by the time required to induce tail-flick after applying radiant heat to the skin of the tail. The latency of reflexive removal of the tail from the heat was measured automatically to the nearest 0.01 s. Tail-flick latency was measured five times, and the basal latency was defined as the mean. Tail-flick data were expressed as percentage change calculated by the formula: (trial latency−baseline latency)/(baseline latency)×100%. Finally, PE-10 catheter position from each animal was confirmed when lumbar enlargement segments were removed for western blot analysis.

PCR analysis of PSD-95/SAP90 in rat spinal cord. The cDNA sequences encoding portions of the PSD-95/SAP90 were amplified using the following synthetic OND primers: PSD1 (5'-CAAGCCCAGCAATGCCTA-3'; SEQ ID NO: 3) and PSD2 (5'-CTTGTCGTAATCAAACAG-3'; SEQ ID NO: 4) for amplification of PSD-95/SAP90 codon positions 789-1525. RNA samples (1 μg) from rat spinal cord, brain and muscle were reverse transcribed to generate first-strand cDNA. The PCR reactions were performed for 25 cycles. Each cycle included 30 s at 94° C., 30 s at 55° C., and 30 s at 71° C. The PCR products were directly cloned into the TA cloning vector (Invitrogen Co., San Diego, Calif., USA) and verified by automatic DNA sequencing.

Fusion protein construction and preparation. cDNA sequence encoding portion of PSD-95/SAP90 was amplified by PCR and subcloned in-frame into PGEX-2T (GIBCO, Rockville, Md., USA) via the BamHI and EcoRI restriction digest sites. The construct was then transformed into BL21 bacteria, and following an induction of expression with isopropyl-β-D-thiogalactopyranoside, the protein was purified under denaturing conditions using glutathione-coupled agarose. The above protein was analyzed by SDS-PAGE followed by coomassie blue staining.

Isolation of PSD fraction. PSD fraction was prepared according to procedures described by Luo et al[11] with modifications. In brief, the spinal cord and brain from male Sprague-Dawley rats were homogenized and centrifuged at 800×g for 10 min to recover the supernatant S1 and the pellet P1. The S1 fraction was subjected to centrifugation at 7,100×g for 15 min to obtain the pellet P2 and the supernatant S2. P2 was resuspended and again subjected to centrifugation at 8,200×g for 15 min to recover the synaptosomal fraction P2'. The P2' fraction was treated with an osmotic shock by diluting with double-distilled water and further centrifuged at 25,000×g for 20 min to generate the pellet LP1 and the supernatant LS1. LP1 was resuspended and centrifuged at 33,000×g for 20 min.

The pellet LP1P was resuspended and loaded onto a discontinuous sucrose gradient composed of 0.10, 1.5 and 2.0 M sucrose. After ultracentrifugation at 208,000×g for 2 h, the PSD fraction was recovered at the interface between 0.5 and 2.0 M sucrose. The PSD fraction was finally resuspended and centrifuged at 208,000×g for 30 min. The recovered the pellet, resuspended in buffer, was considered as the purified PSD fraction.

Co-immunoprecipitation and immunoblotting. About 2-4 μg of the affinity-purified mouse PSD-95/SAP90 antibody (Upstate Biotechnology, Lake Placid, N.Y., USA) was preincubated with 100 μl of a 1:1 slurry of protein A-sepharose for 1 h, and the protein-antibody complex was spun down at 2,000 rpm for 4 min. The solubilized PSD fraction (400 μg) was then added to the sepharose beads and the mixture incubated for 2-3 h at 4° C. The mixture was washed once with 1% TritonX-100 in immunoprecipitation buffer (137 mM NaCl, 2.7 mM KCl, 4.3 mM $Na_2HPO_4$, 1.4 mM $KH_2PO_4$, 5 mM EGTA, 1 mM sodium vanadate, 10 mM sodium pyrophosphate, 50 mM NaF, 20 U/ml Trasylol, and 0.1 mM phenylmethylsulfonyl fluoride), twice with 1% TritonX-100 in immunoprecipitation buffer plus 300 mM NaCl, and three times with immunoprecipitation buffer. The proteins were separated by SDS-PAGE and transferred to a polyvinylidene difluoride membrane. In the control groups, PSD-95/SAP90 antibody was substituted with normal mouse serum, or was preincubated with excess of PSD-95/SAP90 fusion protein (100 μg/ml). Immunoblotting was carried out as described by Lau et al[10]. Individual proteins were detected with the use of primary antibodies to PSD-95/SAP90 (1:1000), NMDA receptor subunits 2A/2B (1:200, Chemicon International Inc, Temecula, Calif., USA), nNOS (1:2000, Santa Cruz Biotechnology Inc., Santa Cruz, Calif., USA), eNOS (1:500, Transduction Lab., Lexington, Ky., USA) and SAP102 (gift from Dr. R. L. Huganir).

Immunocytochemistry. Rats were perfused with 4% paraformaldehyde in 0.1M phosphate-buffered saline (PBS). The spinal cord was harvested and postfixed at 4° C. for 4 h, and cryoprotected in 30% sucrose overnight. Sections (30 μm) were cut on a cryostat and then blocked for 1 h in PBS containing 10% goat serum and 0.3% TritonX-100. Primary antibody to PSD-95/SAP90 (1:1000) was diluted into blocking reagent and incubated with sections overnight. Immunoperoxidase histochemistry was performed using the ABC method. Control sections lacking primary antiserum were stained in parallel.

Example 5

This example demonstrates the decrease in threshold for isoflurane caused by inhibition of expression of PSD 95.

The value for isoflurane MAC in the control (saline-treated) group was 1.16±0.08, which is consistent with that in the previous studies.[49,52] In the groups treated with the antisense ODNs at the doses of 12.5, 25 and 50 μg, the isoflurane MACs were decreased from isoflurane control MAC of 1%, 18% (P<0.01) and 44% (P<0.01), respectively (Table 1). In contrast, intrathecal administration of sense ODN at the dose of 50 μg or missense ODN at the dose of 50 μg did not significantly change the value for isoflurane MAC compared to the control group (Table 1).

No untoward effects were observed in any of the treated animals including the antisense groups. In the ODN-treated groups, there was no significant change in either blood pressure or heart rate compared to control group before the tail clamp (Table 2). Control baseline blood pressure was 119.86±10.58 mmHg systolic and 106.36±7.78 mmHg diastolic, and control baseline heart rate was 513.00±40.28 beats/min.

Example 6

This example demonstrates that antisense ODN reduces the threshold for isolfurane, even in the presence of NMDA which increases the threshold for isoflurane.

In the saline-treated group, intrathecal NMDA at a dose of 1.25 μg caused an increase from isoflurane control MAC by 15% (P<0.01; FIG. 1). The NMDA-induced change in isoflurane MAC was accompanied by a significant increase in systolic and diastolic blood pressures (135.70±3.38 mmHg and 118.30±7.81 mmHg, respectively. P<0.05 vs control) but not in heart rate (529.20±55.20 beats/min, P>0.05 vs control). However, in the group pretreated with 50 μg of antisense ODN, intrathecal administration of 1.25 μg of NMDA did not result in a significant increase in isoflurane MAC compared to the group treated with 50 μg of antisense ODN alone (P>0.05, FIG. 1). Interestingly, in the group pretreated with 50 μg antisense ODN, intrathecal NMDA at a dose of 1.25 μg still produced a significant increase in systolic and diastolic blood pressures (138.00±5.77 mmHg and 117.00±6.35 mmHg, respectively. P<0.05 vs 50 μg antisense ODN-treated group alone) but not in heart rate (553±17 beats/min, P>0.05 vs control).

Example 7

This example demonstrates that antisense ODN did not affect locomotor function.

As shown in Table 3, ODNs with or without NMDA at the doses used in the present study did not produce significant effects on locomotor function. Convulsions and hypermobility were not observed in any of the treated animals including antisense ODN groups. In addition, there was no significant difference in general behaviors including spontanous activity between the control and the ODN-treated groups.

Example 8

This example demonstrates the materials and methods used in examples 5-7.

The present study protocol was approved by the Animal Care Committee at the Johns Hopkins University. Male Sprague-Dawley rats (250-300 g) were housed individually in cages on a standard 12 h-12 h light-dark cycle. Water and food were available ad libitum until rats were transported to the laboratory approximately 1 h before the experiments. All experiments were performed under the same conditions.

Animal Preparation

Rats were anesthetized by intraperitoneal injection of pentobarbital sodium (45 mg/kg). Chronic intrathecal catheters were inserted by passing a polyethylene-10 (PE-10) catheter through an incision in the atlanto-occipital membrane to a position 8 cm caudal to the cisterna at the level of the lumbar subarachnoid space using the methods described previously.[27] The animals were allowed to recover for 5-7 days before experiments were initiated. Rats that showed neurological deficits postoperatively were removed from the study.

To examine whether the deficiency of PSD-95/SAP90 affected the threshold for isoflurane anesthesia, we made an antisense oligodeoxyribonucleotide (ODN) corresponding to the PSD-95/DLG/Z0-1 (PDZ) domain nucleotides 241 to 258 (5'-TGTGATCTCCTCATACTC-3'; SEQ ID NO: 1) of rat PSD95/SAP90 mRNA, as well as the sense ODN and missense ODN (5'-AAGCCCTTGTTCCCATTT-3'; SEQ ID NO: 2).[49] All of the ODNs were searched to exclude non-specificity of the sense or antisense ODNs and to show that missense ODN did not match any confounding sequences in the GenBank database (GenBank accession number M96853). The ODNs were dissolved in saline before administration. As described in the previous work,[49] the rats were injected intrathecally with saline (10 μl) (control), antisense ODNs (12.5, 25, 50 μg/10 μl), sense ODN (50 μg/10 μl) and missense ODN (50 μg/10 μl), respectively, followed by an injection of 10 μl of saline to flush the catheter, every 24 h for 4 days.

Measurement of MAC

On the fifth day after saline or ODNs injection, each rat was placed in a clear plastic cone and anesthetized with 5% isoflurane in oxygen for three to five minutes. After tracheostomy, the trachea of each animal was intubated with a 16-gauge polyethylene catheter. The inspired isoflurane concentration was reduced to 2%, and the animals breathed spontaneously until cannulation of a carotid artery and a jugular vein with PE-50 tubing was accomplished. The isoflurane concentration was decreased further to 1.5%, and ventilation was controlled by a Harvard Animal Respirator (Harvard Apparatus, South Natick, Mass.) adjusted according to the measurement of arterial blood gases to maintain normal partial pressure of oxygen ($P_{O2}$=91-94 mmHg), partial pressure of carbon dioxide ($P_{CO2}$=33-41 mmHg) and pH (7.4-7.44). Electrocardiography and systolic and diastolic blood pressure were monitored using a Grass Polygraph (Astroumed Grass, Quincy, Mass.) and Gould Pressure Transducer (Gould, Cleveland, Ohio). Rectal temperature was maintained between 36.5 and 37.5° C. by use of a heating blanket and warming lights.

A PE-10 catheter was introduced through and beyond the endotracheal tube until obstruction to passage was met and then withdrawn 1 to 2 mm. For isoflurane MAC measurement, the PE-10 catheter was connected to a parameter airway gas monitor (Datex-Engstrom, Inc., Tewksbury, Mass.). After stabilizing about 30 minutes, MAC was measured according to the methods described previously[34] using a long hemostat (8-inch Rochester Dean Hemostatic Forceps) clamped to the first ratchet lock on the tail for 1 min. The tail was always stimulated proximal to a previous test site. Gross movement of the head, extremities, or body was taken as a positive test result, whereas grimacing, swallowing, chewing, or tail flick were considered negative results. The isoflurane concentration was reduced in decrements of 0.12 to 0.15% until the negative response became positive, with 12-15 min equilibration allowed after changes in concentration.[50,51] The MAC was considered to be the concentration midway between the highest concentration that permitted movement in response to the stimulus and the lowest concentration that prevented movement. Finally, intrathecal PE-10 catheter position from each animal was confirmed.

In some saline-treated rats, after initial baseline MAC determination, NMDA at the dose of 1.25 μg [38] or saline was injected intrathecally in a volume of 10 μl saline, followed by an injection of 10 μl saline to flush the catheter. Fresh NMDA solution was prepared for each experiment. An isoflurane concentration was chosen at which movement did not occur in the last negative response before the positive test response. At this isoflurane concentration, 10 min after the intrathecal injection of NMDA, the animals were tested again for reactivity to tail clamp. The concentration of isoflurane was increased, and response to tail clamp was checked every 12-15 min thereafter until a negative response was achieved. In some antisense ODN (50 μg)-treated rats, after initial MAC determination, NMDA or saline was also administered intrathecally. The MAC for isoflurane was again determined following the aforementioned procedures.

Tests of Locomotor Function

The effects of ODNs on locomotor function were examined using the following methods.[52] The animals were organized randomly into six groups: control (saline); 12.5 μg antisense ODN; 25 μg antisense ODN; 50 μg antisense ODN; 50 μg sense ODN; 50 μg missense ODN. The rats were pretreated with ODNs or saline in the manner described above. On the fifth day, 10 μl of saline was injected intrathecally for each rat. In some saline or antisense ODN (50 μg)-treated rats, fresh NMDA solution (1.25 μg/10 μl) was injected intrathecally. The following tests were performed with the experimenter blind to which group was treated with the agents: (1) Placing reflex: The rat was held with the hind limbs slightly lower than the forelimbs, and the dorsal surfaces of the hind paws were brought into contact with the edge of a table. The experimenter recorded whether the hind paws were placed on the table surface reflexively; (2) Grasping reflex: The rat was placed on a wire grid and the experimenter recorded whether the hind paws grasped the wire on contact; (3) Righting reflex: The rat was placed on its back on a flat surface and the experimenter noted whether it immediately assumed the normal upright position. Scores for placing, grasping and righting reflexes were based on counts of each normal reflex exhibited in five trials. In addition, the rat general behaviors including spontaneous activity were observed.

Statistical Analysis

The MAC data were assessed statistically by an analysis of variance. Intergroup differences were analyzed using the Newman-Keuls test. Locomotor data were assessed by a rank sum test. All data are reported as the mean±SD. Significance was set at $P<0.05$.

Example 9

This example demonstrates the role of PSD95 in formalin-induced pain, which is a model for inflammatory-induced pain.

Pretreatment with PSD-95 antisense ODN produced significant decreases in formalin-induced pain behaviors and c-fos expression in the spinal cord. Intrathecal antisense ODN at 50 μg reduced the number of flinches and shakes evoked by formalin by 59% ($p<0.01$) in the tonic period but not in the phasic period. At the same dose, the antisense ODN also decreased the number of Fos-like immunoreactive neurons per section by 48% ($p<0.05$). However, the antisense ODN at 12.5 and 25 μg failed to produce significant changes in the number of flinches and shakes in the phasic and tonic periods, or in the number of Fos-like immunoreactive neurons, when compared to the saline-treated group. Similarly, the sense ODN- and the missense ODN-treated groups did not show any significant difference in the number of flinches and shakes in either period, when compared to the saline-treated group.

These results demonstrate that PSD-95 antisense significantly reduced formalin-induced nociceptive behaviors in the tonic period but not in the phasic period. This suggests that PSD-95 protein may play a key role in the spinal sensitization induced by subcutaneous formalin injection.

All of the experiments were carried out with the approval of the Animal Care Committee at the Johns Hopkins University.

Thirty-eight male Sprague-Dawley rats (250-300 g, Hilltop Laboratory Animals, Scottsdale, Pa., USA) were implanted with an intrathecal PE-10 catheter at the rostral level of the spinal cord lumbar enlargement according to the method described by Yaksh and Rudy. After 4 to 7 days of recovery, they were intrathecally injected with one of the following agents every 24 hours for 4 consecutive days: saline (10 μl, n=6), PSD-95 antisense oligodeoxynucleotide (ODN) (12.5 μg/10 μl, n=6; 25 μg/10 μl, n=6; 50 μg/10 μl, n=6), sense ODN (50 μg/10 μl, n=5) or missense ODN (50 μg/10 μl, n=9). On the fifth day, formalin (4%, 100 μl) was injected into one of the hindpaws. The number of flinches and shakes of the injected paw was assessed for 1 hour. The observational session was divided into phasic (0-10 min) and tonic (10-60 min) periods. Rats were sacrificed two hours after formalin injection and their lumbar spinal cords were harvested for c-fos immunohistochemistry.

Data were assessed as mean±SD. Behavioral test and immunohistochemistry results were assessed by ANOVA. Post-hoc testing was conducted using Bonferroni test. Significance was set at $p<0.05$.

Example 10

This example demonstrates that halothane inhibits the NMDA receptor signaling pathway by inhibiting PDZ domain interactions between PSD-95 or PSD-93 and NMDA receptors or nNOS.

Under normal conditions, PSD-95 interacts with nNOS, resulting in good growth of the yeast carrying pGAD424-PSD-95 and pGBT9-nNOS in –LTH medium. We found that halothane dose-dependently inhibited the growth of the yeast in –LTH media. Treatment with low halothane concentrations (0.4%-0.7%) slowed the growth of yeast clones. At high concentration (1.3%), halothane completely inhibited yeast growth. A similar phenomenon was observed in the growth of the yeast carrying pGAD424-PSD-95 and pGBT9-2B. The growth of the yeast carrying pGAD424-PSD-93 and pGBT9-nNOS or 2B was also inhibited by halothane in a similar way. However, when these yeast clones grew in –LT instead of –LTH media in the presence of high halothane concentration (3.6%), growth did not differ from yeast grown without halothane. This finding suggests that halothane is not cytotoxic to yeast. Rather, the failure of yeast to grow in –LTH media in the presence of halothane must be due to disruption of protein-protein interactions by halothane. In addition, we used a biochemistry approach to demonstrate that halothane blocks GST-fusion PSD-95 or PSD-93 protein from binding to rat brain NMDA receptors or to nNOS. These findings confirm the yeast two-hybrid results.

We utilized the yeast two-hybrid system to investigate the effects of halothane on protein interactions within the NMDA receptor signaling complex. The PDZ domain of nNOS or the C-terminus of NMDA receptor subunit 2B (NR2B) was fused in frame with the GAL4 DNA-binding domain in a yeast vector, pGBT9. The PDZ domain of PSD95 or PSD-93 was fused in frame with the GAL4 activation domain in another yeast vector, pGAD424. Both yeast vectors were co-transformed into the Y190 yeast strain, which was then grown in the absence or presence of halothane at clinically relevant concentrations. Protein-protein interactions were confirmed by both yeast growth on –Leu/–Trp/–His (–LTH) medium and lacz expression. To confirm the yeast two-hybrid results, the GST fusion protein binding assay was performed. The GST-fusion proteins, consisting of the second PDZ domain of PSD-95 or PSD-93, were expressed in bacterial BL21 cells and purified using glutathione-coupled agarose. After preincubation with or without different concentrations of halothane, GST-PSD-95 or GST-PSD-93 was incubated with membrane proteins from rat hippocampus at room temperature for 1 h. After extensive washing, the bound proteins were eluted by boiling in 1×SDS-PAGE sample buffer and detected by immunoblotting.

Utilizing both the yeast two-hybrid system and protein binding assays, we found that halothane dose-dependently inhibited protein interactions of PSD-95/NMDA receptor, PSD-95/nNOS, PSD-93/NMDA receptor and PSD-93/nNOS at physiological concentration. These protein interconnections within the NMDA receptor signaling complex are believed to be critical for excitatory synaptic signal transduction. Disruption of the signal complex may shed light on a novel mechanism for general anesthesia.

Example 11

This example demonstrates the interaction of PSD-95/SAP90 with NMDA receptor and neuronal nitric oxide synthase (nNOS) were examined.

We probed RNA from tissures of the spinal cord, other regions of brain (as positive control) and muscle (as negative control) for messages encoding the PSD-95/SAP90 protein with the use of RT-PCR analysis. A 0.735 Kb mRNA was detected in the spinal cord and the regions of brain but not in muscle. The PCR product was directly cloned into the TA cloning vector and verified as PSD-95/SAP90 by automatic DNA sequencing. PSD-95/SAP90 protein also was found to enrich in the postsynaptic density fraction of the spinal cord. Moreover, immunohistochemistry showed that PSD-95/SAP90 was distributed mainly in spinal superficial laminae, where PSD-95/SAP90 overlapped with NMDA receptor subunits 2A/2B (NR2A/2B) and nNOS, suggesting that PSD-95/SAP90 might interact with NR2A/2B and nNOS in the spinal cord. This was confirmed with the use of co-immunoprecipitation, demonstrating that the PSD-95/SAP90 antibody was able to immunoprecipitate not only PSD-95/SAP90 but also NR2A/2B and nNOS in vivo. In contrast, endothelial NOS was not immunoprecipitated with PSD-95/SAP90 antibody. The area-specific expression of PSD-95/SAP90 and its interaction with NMDA receptor and nNOS in the spinal cord in the present study suggest PSD-95/SAP90 may have important implications for the mechanisms of nociceptive processing.

Example 12

This examples demonstrates the role of PSD-95/SAP90 in chronic neuropathic pain.

The effect of the deficiency of PSD-95/SAP90 on mechanical and thermal hyperalgesia in a rat neuropathic pain model was observed. The antisense oligonucleotide (OND) specifically against PSD-95/SAP90 was employed to reduce the expression of PSD-95/SAP90 in spinal cord. The rats were injected intrathecally with saline (10 µl), antisense OND (50 µg/10 µl) or sense OND (50 µg/10 µl) every 24 h for 4 days. The unilateral L5 spinal nerve was ligated. Hind paw withdrawal response to mechanical or heat stimuli was conducted 1 day prior to the surgery and at 3, 5, 7 and 9 days postoperatively. In the saline-treated group, mechanical and thermal hyperalgesia developed within 3 days and persisted for 9 days or longer. The pretreatment of antisense but not sense ODN resulted in a significant delay of the onset of the mechanical and thermal hyperalgesia. Our results indicate that the deficiency of PSD-95/SAP90 delayed the development of the neuropathic pain. PSD-95/SAP90 is likely involved in the molecular mechanism of the production of hyperalgesia in neuropathic pain triggered via NMDA receptor activation.

REFERENCES

1. Aanonsen L. M., Lei S., and Wilcox G. L. (1990) Excitatory amino acid receptors and nociceptive neurotransmission in rat spinal cord. *Pain* 41, 309-321.
2. Brenman J. E., Christopherson K. S., Craven S. E., McGee A. W. and Bredt D. S. (1996) Cloning and characterization of postsynaptic density 93, a nitric oxide synthase interacting protein. *J. Neurosci.* 16, 7407-7415.
3. Brenman J. E., Chao D. S., Gee S. H., McGee A. W., Craven S. E., Santillano D. R., Wu Z., Huang F., Xia H., Peters M. F., Froehner S. C. and Bredt D. S. (1996) Interaction of nitric oxide synthase with the postsynaptic density protein PSD-95 and α1-syntrophin mediated by PDZ domains. *Cell* 84, 757-767.
4. Cho K. O., Hunt C. A. and Kennedy M. B. (1992) The rat brain postsynaptic density fraction contains a homology of the drosophila discs-large tumor suppressor protein. *Neuron* 9, 929-942.
5. Christopherson K. S., Hillier B. J., Lim W. A. and Bredt D. S. (1999) PSD-95 assembles a ternary complex with the N-methyl-D-aspartic acid receptor and a bivalent neuronal NO synthase PDZ domain. *J. Biol. Chem.* 274, 27467-27473.
6. Kim E., Cho K. O., Rothschild A. and Sheng M. (1996) Heteromultimerization and NMDA receptor-clustering activity of chapsyn-110, a member of the PSD-95 family of proteins. *Neuron* 17, 103-113.
7. Kistner U., Wenzel B. M., Veh R. W., Cases-Langhoff C., Garner A. M., Appeltauer U., Voss B., Gundelfinger E. D. and Garner C. C. (1993) SAP90, a rat presynaptic protein related to the product of the drosophila tumor suppressor gene dig-A. *J. Biol. Chem.* 268, 4580-4583.
8. Kolhekar R., Meller S. T. and Gebhart G. F. (1993) Characterization of the role of spinal N-methyl-D-aspartate receptors in thermal nociception in the rat. *Neuroscience* 57, 385-395.
9. Kornau H. C., Schenker L. T., Kennedy M. B. and Seeburg P. H. (1995) Domain interaction between MDA receptor subunits and the postsynaptic density protein PSD-95. *Science* 269, 1737-1740.
10. Lau L.-H., Mammen A., Ehlers M. D., Kindler S., Chung W. J., Garner C. C. and Huganir R. L. (1996) Interaction of the N-methyl-D-aspartate receptor complex with a novel synapse-associated protein, SAP-102. *J. Biol. Chem.* 271, 21622-21628.
11. Luo J., Wang Y., Yasuda R. P., Dunah A. W. and Wolfe B. W. (1997) The majority of N-mehtyl-D-aspartate receptor complexes in adult rat cerebral cortex contain at least three different subunits. *Mol. Pharmacol.* 51, 79-86.
12. Marvizon J. C., Martinez V., Grady E. F., Bunnett N. W. and Mayer E. A. (1997) Neurokinin 1 receptor internalization in spinal cord slices induced by dorsal root stimulation is mediated by NMDA receptors. *J. Neurosci.* 17, 8129-36
13. Meller S. T., Dykstra C. and Gebhart G. F. (1992) Production of endogenous nitric oxide and activation of soluble guanylate cyclase are required for N-methyl-D-aspartate-produced facilitation of the nociceptive tail-flick reflex. *Eur. J. Pharmacol.* 214, 93-96.
14. Meller S. T., Dykstra C. and Gebhart G. F. (1996) Acute thermal hyperalgesia in the rat is produced by activation of N-methyl-D-aspartate receptors and protein kinase C and production of nitric oxide. *Neuroscience* 71, 327-335.

15. Meller S. T. and Gebhart G. F. (1993) Nitric oxide (NO) and nociceptive processing in the spinal cord. *Pain* 52, 127-136.
16. Migaud M., Charlesworth P., Dempster M., Webster L. C., Watabe A. W., Makhinson M., He Y., Ramsay M. F., Morris R. G., Morrison J. H., O'Dell T. J. and Grant S. G. (1998) Enhanced long-term potentiation and impaired learning in mice with mutant postsynaptic density-95 protein. *Nature* 396, 433-439.
17. Muller B. M., Kistner U., Kindler S., Chung W. J., Kuhlendahl S., Fenster S. D., Lau L. F., Veh R. W., Huganir R. L., Gundelfinger E. D. and Garner C. C. (1996) SAP102, a novel postsynaptic protein that interacts with NMDA receptor complexes in vivo. *Neuron* 17, 255-265.
18. Myers K. J. and Dean N. M. (2000) Sensible use of antisense: how to use oligonucleotides as research tools. *TiPS* 21, 19-23.
19. Nakanishi S. (1992) Molecular diversity of glutamate receptors and implications for brain function. *Science* 258, 597-603.
20. Niethammer M., Kim E. and Sheng M. (1996) Interaction between the C terminus of NMDA receptor subunits and multiple membranes of the PSD-95 family of membrane-associated guanylate kinase. *J. Neurosci.* 16, 2157-2163.
21. Randic M., Jiang M. C. and Cerne R. (1993) Long-term potentiation and long-term depression of primary afferent neurotransmission in the spinal cord. *J. Neurosci.* 13, 5228-5241.
22. Rustioni A. and Weinberg R. J. (1989) The somatosensory system. In: Handbook of Chemical Neuroanatomy (Bjorklund A, Hokfelt T, Swanson L W, eds), pp 219-321. Amsterdam: Elsevier.
23. Sattler R., Xiong Z., Lu W.-Y., Hafner M., MacDonald J. F. and Tymianski M. (1999) Specific coupling of NMDA receptor activation to nitric oxide neurotoxicity by PSD-95 protein. *Science* 284, 1845-1848.
24. Siegan J. B. and Sagen J. (1995) Attenuation of NMDA-induced spinal hypersensitivity by adrenal medullary transplants. *Brain Res.* 680, 88-98.
25. Tao Y.-X., Hassan A., Haddad E. and Johns R. A. (2000) Expression and action of cyclic GMP-dependent protein kinase Iα in inflammatory hyperalgesia in rat spinal cord. *Neuroscience* 95, 525-533.
26. Woolf C. J. and Thompson S. W. N. (1991) The induction and maintenance of central sensitization is dependent on N-methyl-D-aspartic acid receptor activation: implications for the treatment of post-injury pain hypersensitivity states. *Pain* 44, 293-299.
27. Yaksh T. L. and Rudy T. A. (1976) Analgesia mediated by a direct spinal action of narcotics. *Science* 192, 1357-1358.
28. Yung K. K. (1998) Localization of glutamate receptors in dorsal horn of rat spinal cord. *Neuroreport* 9, 1639-1644
29. Aanonsen L M, Wilcox G L: Nociceptive action of excitatory amino acids in the mouse: effects of spinally administered opioids, phencyclidine and sigma agonists. J Pharmacol Exp Ther 1987; 243: 9-19.
30. Dickenson A H, Aydar E: Antagonism at the glycine site on the NMDA receptor reduces spinal nociception in the rat. Neurosci Lett 1991; 121: 263-266.
31. Kuroda Y, Strebel S, Rafferty C, Bullock R: Neuroprotective doses of N-Methyl-D-aspartate receptor antagonists profoundly reduce the minimum alveolar anesthetic concentration (MAC) for isoflurane in rats. Anesth Analg 1993; 77: 795-800.
32. Ishizaki K, Yoon D M, Yoshida N, Yamazaki M, Arai K, Fujita T: Intrathecal administration of N-Methyl-D-aspartate receptor antagonist reduces the minimum alveolar anesthetic concentration of isoflurane in rats. Br J Anaesth 1995; 75: 636-638.
33. Ishizaki K, Yoshida N, Yoon D M, Yoon M H, Sudoh M, Fujita T: Intrathecally administered NMDA receptor antagonists reduce the MAC of isoflurane in rats. Can J Anaesth 1996; 43: 724-730.
34. Davies S N, Lodge D: Evidence for involvement of N-methyl-D-aspartate receptors in 'wind-up' of class 2 neurons in the dorsal horn of the rat. Brain Res 1987; 424: 402-406.
35. Dickenson A H, Sullivan A F: Evidence for a role of the NMDA receptor in the frequency dependent potentiation of deep dorsal horn neurons following C-fiber stimulation. Neuropharmacology 1987; 26: 1235-1238.
36. Dougherty P M, Willis W D: Enhancement of spinalthalamic neuron responses to chemical and mechanical stimuli following combined micro-iontophoretic application of N-methyl-D-aspartic acid and substance P. Pain 1991; 47: 85-93.
37. Malmberg A B, Yaksh T L: Hyperalgesia mediated by spinal glutamate or substance P receptor blocked by spinal cyclooxygenase inhibition. Science 1992; 257: 1276-1279.
38. Kawamata T, Omote K: Activation of spinal N-methyl-D-aspartate receptors stimulates a nitric oxide/cyclic guanosine 3,5-monophosphate/glutamate release cascade in nociceptive signaling. Anesthesiology 1999; 91: 1415-1424.
39. Tao Y X, Johns R A: Activation of cGMP-dependent protein kinase Iα is required for N-methyl-D-aspartate- or nitric oxide-produced spinal thermal hyperalgesia. Eur J Pharmacol 2000; 392: 141-145.
40. Davar G, Hama A, Deykin A, Vos B, Maciewicz R: MK-801 blocks the development of thermal hyperalgesia in a rat model of experimental painful neuropathy. Brain Res 1991; 553: 327-330.
41. Mao J, Price D D, Mayer D J, Lu J, Hayes R L: Intrathecal MK-801 and local nerve anesthesia synergistically reduce nociceptive behaviors in rats with peripherial mononeuropathy. Brain Res 1992; 576: 254-262.
42. Ren K, Dubner R: NMDA receptor antagonists attenuate mechanical hyperalgesia in rats with unilateral inflammation of the hindpaw. Neurosci Lett 1993; 163: 22-26.
43. Seltzer Z, Cohn S, Ginzburg R, Behavior in rats by spinal disinhibition and NMDA receptor blockade of injury discharge. Pain 1991; 45: 69-75.
44. Yamamoto T, Shimoyama N, Mizuguchi T: The effect of morphine, MK-801, an NMDA antagonist, and CP-96,345, an NK-1 antagonist, on the hyperalgesia evoked by carrageenan injection in the rat paw. Anesthesiology 1993; 78: 124-133.
45. Kennedy M B: The postsynaptic density at glutamatergic synapses. Trends Neurosci 1997; 20: 264-268.
46. Nagano T, Jourdi H, Nawa H: Emerging roles of Dlg-like PDZ protein in the organization of the NMDA-type glutamatergic synapse. J Biochem 1998; 124: 869-875.
47. Hata Y, Nakanishi H, Takai Y: Synaptic PDZ domain-containing proteins. Neurosci Res 1998; 32: 1-7.
48. O'Brien R J, Lau L F, Huganir R L: Molecular mechanisms of glutamate receptor clustering at excitatory synapses. Curr Opin Neurobiol 1998; 8: 364-369.
49. Tao Y X, Huang Y Z, Mei L, Johns R A: Expression of PSD-95/SAP90 is critical for N-methyl-D-aspartic acid receptor-mediated thermal hyperalgesia in the spinal cord. Neuroscience 2000; 98: 201-206.

50. Tao Y X, Hassan A, Johns R A: Intrathecally administered cGMP-dependent protein kinase Iα inhibitor significantly reduced the threshold for isoflurane anesthesia. Anesthesiology; 2000: 493-499.
51. Eger E I, Saidman L J, Brandstater B: Minimum alveolar anesthetic concentration: A standard of anesthetic potency. Anesthesiology 1965; 26: 756-763.
52. Eger E I: Effect of inspired anesthetic concentration on the rate of rise of alveolar concentration. Anesthesiology 1963; 26: 153-157.
53. Coderre T J, Van Empel I: The utility of excitatory amino acid (EAA) antagonist as analgesic agents. I. Comparison of the antinociceptive activity of various classes of EAA antagonist in mechanical, thermal and chemical nociceptive tests. Pain 1994; 59: 345-352.
54. Pajewski T N, DiFazio C A, Moscicki J C, Johns R A: Nitric oxide synthase inhibitor, 7-nitro indazole and nitroG-L-arginine methyl ester, dose dependently reduce the threshold for isoflurane anesthesia. Anesthesiology 1996; 85: 1111-1119.
55. Hunt C A, Schenker L J, Kennedy M B: PSD-95 is associated with the postsynaptic density and not with the presynaptic membrane at forebrain synapses. J Neurosci 1996; 16: 1380-1388.
56. Valtschanoff J G, Burette A, Wenthold R J, Weinberg R J: Expression of NR2 receptor subunit in rat somatic sensory cortex: synaptic distribution and colocalization with NR1 and PSD-95. J Comp Neurol 1999; 410: 599-611.
57. Garcia R A, Vasudevan K, Buonanno A: The neuregulin receptor ErbB-4 interacts with PDZ-containing proteins at neuronal synapses. Proc Natl Acad Sci USA 2000; 97: 3596-601.
58. Coote J H: The organization of cardiovascular neurons in the spinal cord. Rev Physiol Pharmacol 1988; 110: 147-285.
59. Loewy A D, Spyer K M: Central Regulation of autonomic functions. Oxford, UK: Oxford Uni Press, 1999.
60. Morrison S F, Callaway T A, Milner T A, Reis D J: Glutamate in the spinal sympathetic intermediolateral nucleus: location by light and electron microscopy. Brain Res 1989; 503: 5-15.
61. Morrison S F, Ernsberger P, Milner T A, Callaway T A, Gong A, Reis D J: A glutamate mechanism in the intermediolateral nucleus mediates sympathoexcitatory responses to stimulation of the rostral ventrolateral medulla. Prog Brain Res 1989; 81: 159-169.
62. Hong Y, Henry J L: Glutamate, NMDA and NMDA receptor antagonists: cardiovascular effects of intrathecal administration in the rat. Brain Res 1992; 569: 38-45.
63. West M, Huang W: Spinal cord excitatory amino acids and cardiovascular autonomic responses. Am J Physiol 1994; 267: H865-873.
64. Hong Y, Yashpal K, Henry J L: Cardiovascular responses to intrathecal administration of strychnine in the rat: Brain Res 1989; 169-173.

TABLE 1

Effects of the suppression of the expression of PSD-95/SAP90 in the spinal cord on the N-methyl-p-aspartate-induced thermal hyperalgesia

| | Control | NMDA | MK-801 + NMDA | DNQX + NMDA | AS (25 µg) + NMDA | AS (50 µg) + NMDA | SE (50 µg) + NMDA | MS (50 µg) + NMDA |
|---|---|---|---|---|---|---|---|---|
| ΔTF latency (%) | −1.23 ± 1.48 | −25.84 ± 1.91* | 0.9 ± 3.0*** | −22.6 ± 3.13* | −11.65 ± 2.46**,**** | −4.72 ± 2.49*** | −21.48 ± 1.55* | −20.96 ± 1.68* |

Percentage change of TF latency was calculated as described in the Experimental Procedures.
AS: antisense;
SE: sence;
MS: missense.
Data are presented as mean ± S.E.M. of six to 12 animals in each group.
*P < 0.01 significantly different from control.
**P < 0.05 significantly different from control.
***P < 0.01 significantly different from NMDA alone.
****P < 0.05 significantly different from NMDA alone.

TABLE 2

Effects of Antisense (AS), Sense (SE), and Missense (SE) Oilgodeoxyrlbonucleotides and Saline on Isoflurane MAC, Blood Pressure (BP), and Heart Rate

| | Saline (n = 14) | 12.5 µg AS (n = 6) | 25 µg AS (n = 6) | 50 µg AS (n = 6) | 50 µg SE (n = 6) | 50 µg MS (n = 6) |
|---|---|---|---|---|---|---|
| MAC | 1.16 ± 0.08 | 1.15 ± 0.18 | 0.98 ± 0.14* | 0.72 ± 0.05* | 1.15 ± 0.21 | 1.13 ± 0.15 |
| BP (mmHg) | | | | | | |
| Systolic | 119.86 ± 10.58 | 127.58 ± 11.72 | 122.75 ± 10.81 | 129.58 ± 11.73 | 126.67 ± 10.40 | 121.33 ± 15.84 |
| Diastolic | 106.36 ± 7.78 | 112.58 ± 7.14 | 105.83 ± 7.89 | 112.50 ± 11.20 | 105.58 ± 13.07 | 105.75 ± 11.40 |
| Heart rate (beats/min) | 513.00 ± 40.78 | 534.80 ± 29.13 | 541.20 ± 16.70 | 514.20 ± 62.20 | 529.60 ± 22.61 | 524.70 ± 44.90 |

*P < 0.01 versus saline-treated (control) group.
MAC = minimum alveolar concentration.

TABLE 3

| | Mean (SD) Changes in Locomotor Test | | |
|---|---|---|---|
| Agents | Placing | Grasping | Righting |
| Saline | 5 (0) | 5 (0) | 5 (0) |
| 12.5 μg AS | 5 (0) | 5 (0) | 5 (0) |
| 25 μg AS | 5 (0) | 5 (0) | 5 (0) |
| 50 μg AS | 4.83 (0.41) | 4.67 (0.52) | 4.83 (0.41) |
| 50 μg SE | 5 (0) | 5 (0) | 5 (0) |
| 50 μg MS | 5 (0) | 5 (0) | 5 (0) |
| Saline + 1.25 μg NMDA | 5 (0) | 5 (0) | 5 (0) |
| 50 μg AS + 1.25 μg NMDA | 4.83 (0.41) | 4.83 (0.41) | 4.83 (0.41) |

N = 6, five trials.
AS = antisense;
SE = sense;
MS = missense;
NMDA = N-methyl-D-aspartate.

The invention claimed is:

1. A method for relieving acute or chronic pain comprising:
   administering intrathecally to a human in need thereof an effective amount of an antisense oligonucleotide which is complementary to mRNA encoding human post-synaptic density 95 protein (PSD95), which comprises SEQ ID NO: 1, and which inhibits expression of human PSD95, whereby acute or chronic pain experienced by the human is relieved.

2. A method for treating or inhibiting hyperalgesia comprising:
   administering intrathecally to a human in need thereof an effective amount of an antisense oligonucleotide which is complementary to mRNA encoding human PSD95, which comprises SEQ ID NO:1, and which inhibits expression of human PSD95, whereby hyperalgesia experienced by the human is relieved.

3. A method of reducing a threshold for anesthesia comprising:
   administering intrathecally to a human an anesthetic and an antisense oligonucleotide which is complementary to mRNA encoding human PSD95, which comprises SEQ ID NO:1, and which inhibits expression of human PSD95, wherein the amount of anesthetic administered is less than the amount required in the absence of the antisense oligonucleotide to achieve a desired anesthetic effect, whereby the desired anesthetic effect is achieved.

4. A pharmaceutical formulation comprising an isolated and purified antisense oligonucleotide which is complementary to mRNA encoding human PSD95 and which inhibits expression of human PSD95 and which comprises SEQ ID NO:1.

5. The pharmaceutical formulation of claim 4 wherein the oligonucleotide is manufactured under regulatory-approved conditions for administration to humans.

6. The pharmaceutical formulation of claim 4 wherein the oligonucleotide is pyrogen-free.

7. The method of claim 3 wherein the anesthetic is selected from the group consisting of halothane, isoflurane, desflurane, xenon, and sevoflurane.

8. The method of claim 3 wherein the anesthetic is an inhalational anesthetic.

9. The method of claim 3 wherein the anesthetic is selected from the group consisting of urethane, chloral hydrate, and sodium pentobarbitone.

* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Rattus rattus

<400> SEQUENCE: 1
tgtgatctcc tcatactc                                                 18

<210> SEQ ID NO 2
<211> LENGTH: 18
<212> TYPE: DNA
<213> ORGANISM: Rattus rattus

<400> SEQUENCE: 2
aagcccttgt tcccattt                                                 18

<210> SEQ ID NO 3
<211> LENGTH: 18
<212> TYPE: DNA
<213> ORGANISM: Artificial Sequence
<220> FEATURE:
<223> OTHER INFORMATION: PCR primer

<400> SEQUENCE: 3
caagcccagc aatgccta                                                 18

<210> SEQ ID NO 4
<211> LENGTH: 18
<212> TYPE: DNA
<213> ORGANISM: Artificial Sequence
<220> FEATURE:
<223> OTHER INFORMATION: PCR primer

<400> SEQUENCE: 4
cttgtcgtaa tcaaacag                                                 18